United States Patent [19]

Melzig et al.

[11] Patent Number: 5,801,243
[45] Date of Patent: Sep. 1, 1998

[54] PHOTOCHROMIC COMPOUNDS (7)

[75] Inventors: Manfred Melzig, Wessling; Herbert Zinner, Taufkirchen, both of Germany

[73] Assignee: Optische Werke G. Rodenstock, Munich, Germany

[21] Appl. No.: 393,010

[22] PCT Filed: Jun. 28, 1994

[86] PCT No.: PCT/DE94/00744

§ 371 Date: Feb. 27, 1995

§ 102(e) Date: Feb. 27, 1995

[87] PCT Pub. No.: WO95/00500

PCT Pub. Date: Jan. 5, 1995

[30] Foreign Application Priority Data

Jun. 28, 1993 [DE] Germany .................... 43 21 461.4

[51] Int. Cl.⁶ .................... C07D 265/12; C07D 265/34; C07D 265/36
[52] U.S. Cl. .................... 544/71; 544/95; 544/101; 544/105
[58] Field of Search .................... 544/71, 99, 101, 544/105

[56] References Cited

U.S. PATENT DOCUMENTS 3,562,172 2/1971 Oho et al. .................... 252/600

FOREIGN PATENT DOCUMENTS 449669 10/1991 European Pat. Off. .
87/00524 1/1987 WIPO .

OTHER PUBLICATIONS

Grummt et al, Tetrahedron Letters, vol. 22, No. 40, pp. 3945–3948 (1981).

Nakamura et al, Chem. Abstracts 120: 257519p for JP 05-98,252 (Apr. 20, 1993).

Reichenbaecher et al, Chem. Abst. 98: 135279s for DD 156,372 (Aug. 18, 1982).

Reichenbaecher et al, Chem. Abst. 97: 164536h for DD 153,690 (Jan. 27, 1982).

*Primary Examiner*—Richard L. Raymond
*Attorney, Agent, or Firm*—Antonelli, Terry, Stout & Kraus, LLP

[57] ABSTRACT

Disclosed are photochromic oxazine compounds, yielded by means of condensation of an aldehyde bearing in the α-position to the aldehyde group a halogen or hydroxy group (reacting agent 1), with (substituted) ortho-aminohydroxy aromatic compounds (reacting agent 2).

10 Claims, No Drawings

PHOTOCHROMIC COMPOUNDS (7)

DESCRIPTION

This application is a 371 of PCT/DE94/00744, filed Jun. 28, 1994.

1. Technical Field

The present invention relates to photochromic compounds, in particular, for the tinting of optical elements made of plastic material.

2. State of the Art

Pyrans are a class of photochromic compounds that have been known for some time and have been extensively investigated. For instance, recently developed photochromic dyes such as the diphenyl-naphthopyrans described in U.S. Pat. No. 5,066,818, the PCT publication WO 92/09593 or U.S. Pat. No. 4,818,096 have within wide bounds adjustable kinetic properties. Their lifetime, i.e. their light stability in continuous use is however insufficient for many applications.

Spiropyrans, which are spiro-linked in the 2-position also show insufficient light stability. This is also the case with the adamantan derivatives described in the U.S. Pat. No. 4,818,096 as well as with the derivatives described in U.S. Pat. No. 5,106,998 principally tricyclic hydrocarbons.

The compounds of the class of indolino-(spirobenz- or naphthoxazines) hitherto preferred for their excellent stability such as those, e.g., described in U.S. Pat. No. 3,652,172, U.S. Pat. No. 3,578,602, U.S. Pat. No. 4,215,010 or U.S. Pat. No. 4,637,698 can be minimally influenced with regard to their darkening and lighting speed.

DESCRIPTION OF THE INVENTION

The object of the present invention is to describe photochromic compounds and to provide a mode of synthesis of these compounds having the advantageous properties of pyrans and, in particular of diphenylnaphthopyrans with a lifetime respectively a light stability comparable to that of oxazines known, in particular, from indolinospironaphtho or indolinospirobenz derivatives.

According to the present invention, the object is solved by the condensation of substituted diphenylacetaldehydes (reacting agent 1) with (substituted) ortho-aminohydroxy aromatic compounds (reacting agent 2). This yields a new class of substances having the needed positive properties. Especially preferred is a halogen or hydroxy group which is located in the α-position to the aldehyde group and condenses with the hydroxy group of the reacting agent 2 releasing water or halogen hydrogen. One or both phenyl residues may, of course, also be further substituted.

The reaction can also be conducted with (substituted) dinaphthyl derivatives or phenylnaphthyl derivatives as reacting agent 1; heteroaromatic compounds may also be employed.

Both phenyl rings of reacting agent 1 may also be chemically rigidly linked (e.g., fluorene, dibenzosuberone, anthrone, xanthene or thioxanthene derivatives) as was described in an application filed on the same day of the same applicant.

The kinetic properties of the invented compounds may be influenced in an analogous manner to the method according to WO 92/09593 in particular via subtituents in the 2-position of the aromatic rings of reacting agent 1.

The second reacting agent especially preferably possesses an ortho-amino-hydroxy group at an aromatic ring system. This may be another substituted benzene, naphthalene, phenanthrene, anthracene or, by way of illustration, quinoline respectively isoquinoline from the series of heteroaromatic compounds.

Preferred are 1-amino-2-naphtholes, with the kinetic properties being easily influenced by means of suited substitution in the 3-position analog to U.S. Pat. No. 5,066,818.

The condensation itself can be conducted with the free base, the hydrochloride or with modification of the specifications also with by way of illustration amino groups protected by an acetyl group.

Suited as solvents are, in particular, such solvents that form with water a low-boiling azeotrope so that the reaction water can be easily removed, by way of illustration, by means of a Dean-Stark apparatus. The hydrohalogen is extracted or bound, by way of illustration, in an extractor by a stable alkali hydroxide. Depending on the utilized reacting agents, the reaction is preferably catalyzed with a base or an acid (p-toluol-sulfonic acid).

DESCRIPTION OF PREFERRED EMBODIMENTS

Mode of Synthesis

In the following, a synthesis is described based on 1-amino- 2-naphthol. All the compounds of table 1 were synthesized in an analogous manner. The corresponding nitroso derivatives can also obtained by reducing the nitro derivatives (cf. Liebermann and Jacobson, Ann. 211, 48 (1882)). This mode is disadvantageous because of the predominantly yielded 4-nitro-1-naphthols in the preliminary stage for the compounds 1–3. The analog hydroxy compounds can principally be utilized instead of the halogen acetaldehyde compounds, the yields however are, i.a., distinctly less.

The methyl substituted diphenyl-acetaldehydes respectively naphthylphenyl-acetaldehydes required for compounds 3, 7 and 9 can be represented according to specifications in the literature.

1. Bromification of diphenylacetaldehyde 25 g (0.13 mol) of diphenylacetaldehyde are dissolved with nitrogen scavenging in 100 ml of carbon tetrachloride released of oxygen. The solution is cooled to –5° C. and slowly dripped to 21 g (0.26 mol) of bromine. The temperature should never exceed –3° C. The solution turns brown with the intially rapid bromine tinting distinctly slowing down with time. While heating to about 5° C. the untransformed bromine is extracted with nitrogen until a honey-yellow solution is left. After withdrawl of the CC14, 30.8 g of a yellow oil are yielded.

2. Reduction of nitrosonaphthol 48 g of 1-nitroso-2-naphthol are suspended in a mixture of 300 ml of water and 60 ml of 5n NaOH, then another 240 ml of 5n NaOh are added. While stirring well hot water vapor is passed through the solution until the temperature reaches 35° C. Subsequently 120 g of freshly prepared sodium dithionite is added with the temperature rapidly rising to 60° C. The solution assumes an amber-colored tint. After 15 minutes, the solution is rapidly cooled to under 20° C. by adding 200 g of ice and 100 ml of concentrated hydrochloric acid. The white, flaky precipitation is filtered by vacuum and suspended in a mixture of 500 ml of water and 50 ml concentrated hydrochloric acid. Overheated water vapor is passed into this mixture with such a volume flow that the temperature reaches 90° C. within 10 min. At this temperature is stirred another hour while reducing the vapor flow. The still hot solution is filtered with the aubergine-colored precipitation remaining. Upon cooling the filtrate, a light, flaky precipitation falls out which is sucked away, scavenged with diluted hydrochloric acid and then with ether and dried. Yielded were 45 g of 1-amino-2-naphthol-hydrochloride. The amino-hydroxy aromatic compounds were employed in all the transformations into this acidic form, because the free bases with the exception of 5-amino-6-quinoline proved to be very unstable.

3. Description of the oxazine compound 10 g (51 mmol) of 1-amino-2-naphthol-hydrochloride are boiled with 14 g (53 mmol) of diphenyl-bromacetaldehyde in 200 ml of toluol while adding a spatual tip of p-toluol sulfonic acid and stirring at the water separater. If no further reaction water is formed, the solution is permitted to cool off. After extracting the solvent, the crude product is chromatographed with methylene chloride on aluminium oxide.

The fraction which runs red contains the photochromic compound which shows an intensive red-violet photochromic tinting on the filter paper under UV light. After extraction of the running medium, the product diethyl ether/hexane is recrystallized. Yielded are 5.4 g of a red-tinged powder which was identified by means of NMR analysis as 2,2-diphenyl-2H-naphth(2,1-b)oxazine (example 4).

Fabrication of Measuring Samples

For comparison, analog state of art compounds were synthetized for some of the compounds of table 1. These differ in structure by the exchange of oxazine-nitrogen atoms for a CH residue are therefore pyrans which are analog to oxazines.

Commercial zero lenses made of polydiethylene glycol bisallyl carbonate (diameter 71 mm, center thickness approximately 2 mm) are dyed on their convex side with the invented compounds as well as the reference substances using the process described in DE 35 16 568 A1.

Measurement Results

The produced lenses described in the preceding were measured in a measuring bench according to DIN 58 217. The characteristic value is the spectral light-intensity sensitivity of the normal viewer. The Vλ-valuated difference between the transmission in the faded state $\tau_o$ and the excited state $\tau_e$ after 15 minute exposure to light at 23° C. in a tempered cell is in the ΔOD form the starting value:

$$\Delta OD = 10 \log \tau_o - 10 \log \tau_e.$$

After exposure to approximately 100 klux and a spectral distribution similar to the sun for 100 hours in the radiation test device (Suntest, Original Hanau), this difference is redetermined.
The quotient $$R = (\Delta OD 100 \text{ h}):(\Delta OD \, 0 \text{ h})$$

is the remaining residual power. It relates to the starting value and is a direct reference radiation gage, because all the differences regarding spectral excitation and absorption, dying capability of the plastic material, etc. have no influence. The results are shown in table 2.

TABLE 1

Substitution Scheme of the Invented Photochromic Compounds

| Example | Base | R1 | R2 | R3 | R4 | R5 |
|---|---|---|---|---|---|---|
| 1 | A | H | H | H | H | H |
| 2 | A | H | H | H | H | OCH$_3$ |
| 3 | A | H | 2-CH$_3$ | H | H | H |
| 4 | B | H | H | H | H | H |
| 5 | B | H | H | H | H | OCH$_3$ |
| 6 | B | H | 2-CH$_3$ | H | H | H |
| 7 | B | H | H | OCOCH$_3$ | H | H |
| 8 | B | OCH$_3$ | 2,3-benzo | H | H | H |
| 9 | C | H | H | H | H | H |
| 10 | C | H | H | H | C$_6$H$_5$ | H |
| 11 | D | H | H | H | H | H |
| 12 | E | H | H | H | H | H |

The following shows the structural formula, where the resdiues listed in table 1 are located.

Base:

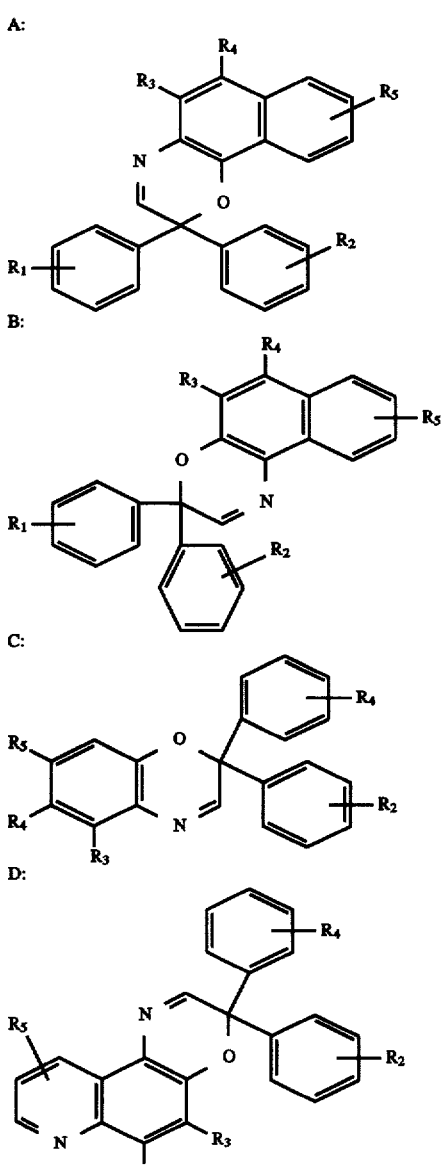

E:

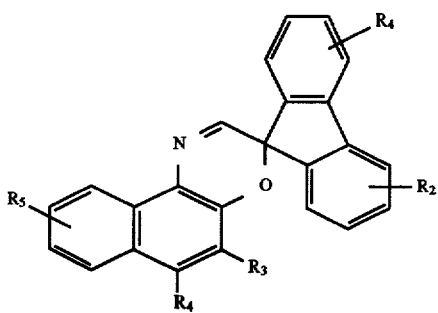

2 gives the lifetime of the individual compounds:

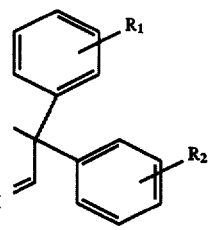

| | X = N | X = CH (state of the art) | |
|---|---|---|---|
| Comp. No. | R (%) | Pat. No. | R (%) |
| 1 | 70 | 1' (US 3.567.605) | 54 |
| 4 | 78 | 4' (US 3.627.690) | 56 |
| 5 | 62 | 5' (WO 93/17071) | 45 |
| 6 | 62 | 6' (WO 92/09593) | 41 |
| 7 | 69 | 7' (US 5.066.818) | 47 |

What is claimed is:

1. A process for the production of photochromic oxazine compounds, characterized by an aldehyde bearing in the λ-position to the aldehyde group a halogen or hydroxy group (reacting agent 1) being condensed with a (substituted) ortho-amino-hydroxy aromatic compound (reacting agent 2).

2. A process according to claim 1, characterized in that said reacting agent 1 is a (substituted) 2-halogen- or 2-hydroxy-diphenyl-or phenyl-naphthyl-or dinaphthylacetaldehyde.

3. A process according to claim 1, characterized in that the aldehyde and the halogen or hydroxy group are located at a carbon atom which is part of a ring system.

4. A process according to claim 3, characterized in that said ring system is fluorene, dibenzosuberone, xanthene or thioxanthene.

5. A process according to claim 3, characterized in that said ring system is an aliphatic (monocyclic carbo or hetero cycle).

6. A process according to claim 5, characterized in that said ring system is cyclohexane or tetrahydropyran.

7. A process according to claim 3, characterized in that said ring system is a polycyclic hydrocarbon such as adamantan, norbornane, norcamphor or fenchone.

8. A process according to claim 1, characterized in that said reacting agent 2 is a (substituted) 1-amino-2-naphthol or 2-amino-1-naphthol.

9. A process according to claim 1, characterized in that said reacting agent 2 is 5-amino-6-hydroxyquinoline or 6-amino-5-hydroxyquinoline.

10. A process according to claim 1, characterized in that said reacting agent 2 is 5-amino-6-hydroxyisoquinoline or 6-amino-5-hydroxyisoquinoline.

* * * * *